United States Patent

Vallelunga et al.

[11] Patent Number: 5,595,566
[45] Date of Patent: Jan. 21, 1997

[54] APPARATUS FOR SHIELDING A SYRINGE NEEDLE

[75] Inventors: Anthony J. Vallelunga, Albany, N.Y.;
Thomas T. Paquin, Shaftsbury, Vt.;
Brian Crawford, Valatie, N.Y.

[73] Assignee: Unique Management Enterprises, Inc., Albany, N.Y.

[21] Appl. No.: 569,800

[22] Filed: Dec. 8, 1995

Related U.S. Application Data

[63] Continuation-in-part of Ser. No. 381,193, Jan. 31, 1995, Pat. No. 5,498,243.

[51] Int. Cl.$^6$ ............................................. A61M 5/32
[52] U.S. Cl. ............................ 604/197; 604/192; 604/110
[58] Field of Search ........................... 604/110, 197, 604/192, 198, 240–243, 905, 187, 263, 195; 128/919

[56] References Cited

U.S. PATENT DOCUMENTS

| | | | |
|---|---|---|---|
| 4,897,083 | 1/1990 | Martell | 604/192 |
| 4,904,244 | 2/1990 | Harsh et al. | 604/187 |
| 4,935,016 | 6/1990 | Deleo | 604/198 |
| 4,998,924 | 3/1991 | Ranford | 604/192 X |
| 5,160,326 | 11/1992 | Talonn et al. | 604/198 |
| 5,211,630 | 5/1993 | Schmahmann | 604/110 |
| 5,242,417 | 9/1993 | Paudler | 604/192 |
| 5,290,255 | 3/1994 | Vallelunga et al. | |
| 5,490,841 | 2/1996 | Landis | 604/110 |

*Primary Examiner*—Corrine M. McDermott
*Assistant Examiner*—V. Alexander
*Attorney, Agent, or Firm*—John A. Merecki

[57] ABSTRACT

A syringe shielding apparatus comprising an adapter having a tubular collar and a flexible snap ring joined by a living hinge, and a needle shield. Radially extending projections, provided on the tubular collar, slide within longitudinally extending slots in the needle shield, allowing the longitudinal extension and retraction of the needle shield relative to the housing of the syringe. The flexible snap ring expands into a groove in the needle shield at extension. Expansion of the snap ring into the groove in the needle shield locks the shield in the extended position over the syringe needle.

8 Claims, 6 Drawing Sheets

FIG. 27
FIG. 28

APPARATUS FOR SHIELDING A SYRINGE NEEDLE

This is a continuation-in-part of U.S. patent application Ser. No. 08/381,193, filed Jan. 31, 1995, entitled APPARATUS FOR SHIELDING A SYRINGE NEEDLE now U.S. Pat. No. 5,498,243.

FIELD OF THE INVENTION

This present invention relates in general to an apparatus for shielding a syringe needle, and more particularly to an apparatus which can be locked in an extended position surrounding and shielding a syringe needle after use of the syringe. The apparatus includes a needle shield and a unique adapter which allows the needle shield to be used with virtually any type of conventional syringe. The adapter includes a tubular collar for securing the adapter about the restricted end of a syringe, and a flexible snap ring for locking the needle shield in an extended position over the syringe needle.

BACKGROUND OF THE INVENTION

Syringes are generally utilized to inject medications and other fluids into the bloodstream of patients. Syringes are also used to aspirate or withdraw various fluids, such as blood, from patients.

When a syringe is used, the contact of the syringe needle with the patient can lead to contamination of the syringe, including the needle, with various contagious micro-organisms. The contaminated syringe and needle then pose a risk to anyone handling the syringe if the person accidentally pricks or contacts themselves or someone else with the contaminated needle.

The danger of infection from contaminated needles and syringes has become of increased concern with the discovery of HIV (human immunodeficiency virus) which causes AIDS (Acquired Immune Deficiency Syndrome). The danger also exists for other infectious diseases and infections, such as hepatitis, streptococcal sepsis, tetanus, tuberculosis, Rocky Mountain Spotted Fever, and malaria.

The problem is especially relevant in the health care industry. Each year, 7% of hospital employees are involved in needle stick injuries, of which 60% are nurses. It is estimated that 57% of accidental needle sticks occur while attempting to recap the needle of a syringe or in disposal of the syringe. It is also estimated that in excess of $28.3 million is spent annually in the United States for the diagnosis and initial treatment of needle sticks.

Various strategies to deal with this problem have been attempted. One approach involves the use of some sort of cap to cover the syringe needle after use, to prevent contact with the needle. This cap can be as simple as the original plastic cap which is used to cover the needle prior to use. However, the motion required to replace the original needle cap allows for error resulting in needle contact. This is due to the relatively small diameter of the cap and the required movement of a hand toward the contaminated needle during cap replacement.

Other approaches provide for additional means for covering the needle, in the form of shields. A highly effective example of a shield is disclosed in U.S. Pat. No. 5,290,255 to Vallelunga et al., entitled APPARATUS FOR SHIELDING A SYRINGE NEEDLE, issued Mar. 1, 1994 and incorporated herein by reference.

The needle shield disclosed in the above-referenced U.S. patent to Vallelunga et al. provides a means for preventing pricks and contact with contaminated needles, without interfering with the normal usage of a syringe. The needle shield is easily manufactured in conjunction with a syringe and/or may be easily assembled onto an existing syringe if manufactured separately.

Other examples of needle shield systems are disclosed in U.S. Pat. No. 4,666,435 (Braginetz, May 1987), U.S. Pat. No. 4,871,355 (Kikkawa, October 1989), U.S. Pat. No. 4,923,447 (Morgan, May 1990),U.S. Pat. No. 5,024,616 (Ogle, II, June 1991), and U.S. Pat. No. 5,059,185 (Ryan, October 1991), each incorporated herein by reference.

Syringe shielding systems generally enclose the body of the syringe within a clear plastic sheath designed to be longitudinally displaced over the syringe needle after use, thereby preventing multiple uses of the needle. During normal usage of the syringe, the sheath encloses a substantial portion of the main body of the syringe, potentially reducing the readability of the underlying dosage indicia. As should be readily apparent, the inability to accurately view the dosage indicia on a syringe may pose serious health threats to a patient if an incorrect dosage of a medication is administered. This problem is especially relevant to those patients, such as diabetics, who are required to accurately self-administer injections.

SUMMARY OF THE PRESENT INVENTION

In order to avoid the disadvantages of the prior art, the present invention provides a needle shield and syringe assembly which is designed to prevent pricks and contact with contaminated needles.

In accordance with a first embodiment of the present invention, the needle shield generally includes a hollow sleeve, a needle shield, and a flexible snap ring. The hollow sleeve is mounted to a syringe housing. Any syringe can be adapted for use with the needle shield, including conventional medical syringes and syringes made for single use only (see, for example, U.S. Pat. No. 5,215,524 to Vallelunga et al., entitled "Plunger For Non-Reusable Syringe", the contents of which are hereby incorporated by reference). The hollow sleeve has one or more radially extending projections and a groove into which the flexible snap ring can be inserted. The hollow sleeve can be molded unitarily with the syringe, or may be permanently secured thereon using any suitable means.

The needle shield is movably positioned on the hollow sleeve surrounding the syringe housing. In an extended position, the needle shield surrounds and shields the needle, while in a retracted position the needle shield leaves the needle exposed for use. To accomplish the movement of the needle shield, it is equipped with one or more longitudinally extending slots. Each of the radially extending projections of the hollow sleeve is slidably disposed within a corresponding slot on the needle shield.

When the snap ring is positioned within the groove on the hollow sleeve, the needle shield can be slid forward (toward and over the needle of the syringe) by pulling the syringe itself back toward the user as the projections of the hollow sleeve track along in the slots. At this time, the inner wall of the needle shield holds the snap ring securely in the groove of the hollow sleeve. When the needle shield is extended to fully cover the syringe needle, the groove on the inner wall of the needle shield is then positioned in line with the snap ring. The flexible snap ring extends outward into the groove in the needle shield, while remaining in part within the groove of the hollow sleeve. The tension forces of the snap ring trying to extend outwardly result in the secure and permanent positioning of the snap ring at this point. The snap ring therefore prevents further movement of the slidable needle shield, since the snap ring has locked into the grooves.

The syringe upon which the shield is utilized, whether it is a conventional medical syringe or a single use syringe, includes a hollow cylindrical syringe housing having an interior, and a hollow needle mounted to the housing. The needle is in fluid communication with the interior of the housing, and fluid can be drawn into the syringe housing or ejected therefrom by moving the plunger means which is positioned within the housing.

The hollow sleeve can be formed as an integral part of a syringe being manufactured, or can be attached to the housing of a syringe manufactured separately. In either case, the snap ring is formed separately from the hollow sleeve, and is attached thereto only after the hollow sleeve has been permanently secured (or unitarily molded) to the syringe housing. Such attachment can be by any suitable permanent means, including glue or heat sealing. Preferably, the various parts of the syringe assembly, including the shield, hollow sleeve, and the snap ring, are made of plastic to allow for manufacturing by injection molding. This allows for efficient and cost-effective production of the syringe and shield. Suitable plastics include clear lexan plastic, since a clear plastic allows the numbers on the syringe to be more easily read through the shield components.

The resulting needle shield and syringe assembly can thus reduce the risk of accidental pricks and contact with contaminated needles. The movement of the needle shield is accomplished by a motion which is not directed toward the tip of the contaminated needle, and can be accomplished smoothly and easily with little effort. Thus, the needle shield and syringe assembly is practical in both manufacturing and usage.

In an alternate embodiment of the present invention, the needle shield further includes an elongated magnifying arrangement, extending longitudinally along a side of the needle shield, for enlarging the dosage indicia imprinted on the underlying syringe housing. The elongated magnifying arrangement may extend completely or partially along the length of the needle shield, depending upon the position and/or characteristics of the dosage indicia on an associated syringe.

In accordance with the present invention, the magnifying arrangement is formed from a clear plastic or another suitable, clear material. Preferably, the magnifying arrangement is of a convex shape, wherein the outwardly curved upper surface of the convex magnifying arrangement provides a magnifying effect. Essentially, the magnifying arrangement appears as a semi- cylindrical protuberance which extends longitudinally along a side of the needle shield. Of course, flat or other non-convex magnifying arrangements may be incorporated into the needle shield without departing from the scope of the present invention.

The magnifying arrangement is preferably formed unitarily with the needle shield from a clear plastic material in a molding process, although it may be formed separately therefrom and attached, either fixedly or removably, to the needle shield in any suitable manner. Advantageously, if a removable magnifying arrangement is utilized, the magnification provided by the present invention may be adjusted as necessary according to the needs of the user, the characteristics of the dosage indicia or other factors.

In yet another embodiment of the present invention, a unique adapter may be used in lieu of the hollow sleeve/snap ring combination to allow the needle shield to be used with virtually any type of conventional syringe. The adapter includes a tubular collar designed to fit over the restricted end of the syringe, and a flexible snap ring, similar to the snap ring described above, designed to expand into the groove in the needle shield as the needle shield is longitudinally displaced over the syringe needle, thereby permanently locking the needle shield over the syringe needle. Unlike the hollow and flexible snap ring of the adapter are permanently joined via a "living hinge". As such, the adapter is easily manufactured as a single unit, is easier to handle, and is more easily secured to the restricted end of the syringe. In this embodiment of the present invention, the flexible snap ring does not have to be carefully positioned relative to the tubular collar. Indeed, one is only required to slide the flexible snap ring and tubular collar over the restricted end of the syringe after bending the ring/collar about the living hinge joining the two components of the adapter together.

BRIEF DESCRIPTION OF THE DRAWINGS

These and other objects, features and advantages of the present invention will be evident from the following detailed description of preferred embodiments when read in conjunction with the accompanying drawings in which.

DETAILED DESCRIPTION OF THE INVENTION

Figures 1, 2, 3, 4, 5:
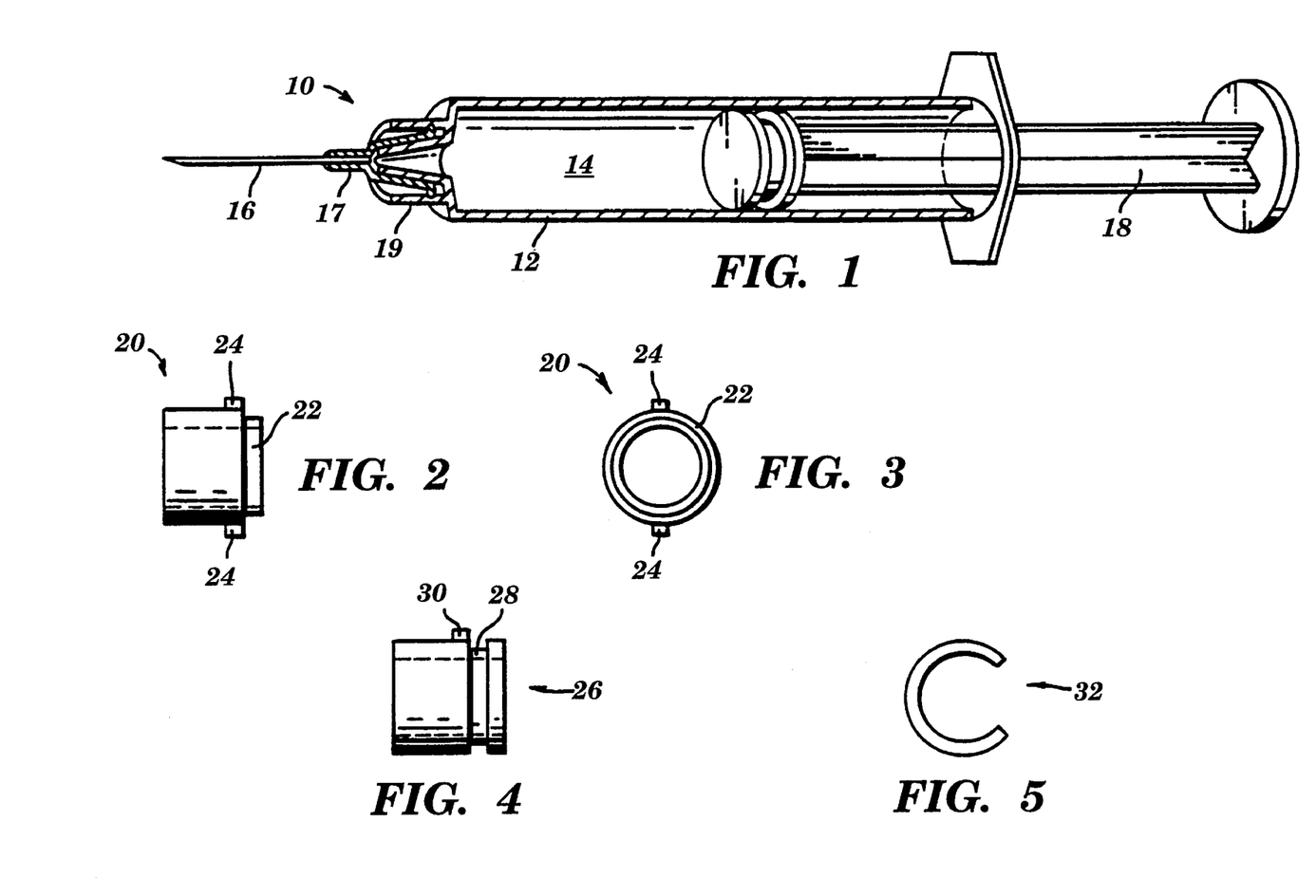
FIG. 1 is a partially cut-away isometric view of a syringe having a needle.
FIG. 2 is a front elevational view of one embodiment of a hollow sleeve according to the subject invention.
FIG. 3 is a right side elevational view of the hollow sleeve shown in FIG. 2.
FIG. 4 is an elevational view of another embodiment of a hollow sleeve according to the subject invention.
FIG. 5 is an elevation view of one embodiment of a snap ring according to the subject invention.

A typical syringe upon which the shield of the subject invention can be used is shown in FIG. 1. The syringe 10 has a hollow cylindrical housing 12 to which a hollow needle 16 is mounted. The hollow needle 16 is in fluid communication with the interior 14 of the housing 12. Movement of a plunger 18 positioned within the housing 12 allows the drawing of fluid into the syringe and the ejecting of fluid from the syringe. Syringe needles are generally marketed with a plastic-type bracket 17 on one end thereof. This plastic-type bracket mounts on the restricted end 19 of the syringe. The bracket may snugly slide over the restricted end, or the restricted end could be provided with grooves into which corresponding ridges on the bracket are twisted. Various means for connecting syringe needles are known in the art and can thus be used in the subject invention to mount a needle to a syringe housing.

Figure 10:
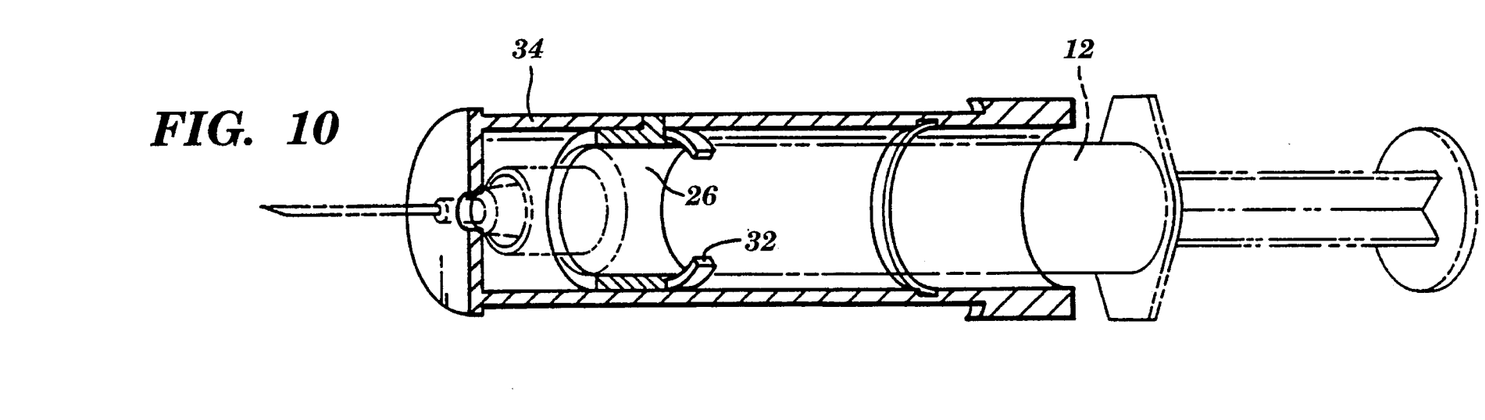
FIG. 10 is a partially cut-away isometric view of a syringe and shield assembly according to another embodiment of the subject invention, with the needle shield in a retracted position.
Figures 11, 12:
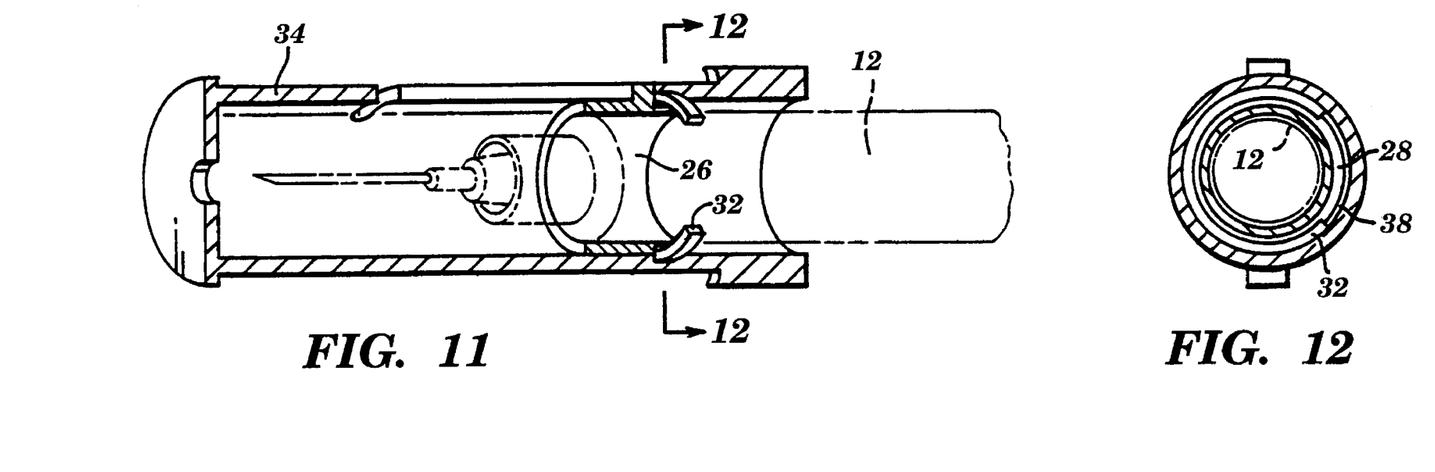
FIG. 11 is a partially cut-away isometric view of the syringe and shield assembly shown in FIG. 10 with the needle shield in an extended position.
FIG. 12 is a cross-sectional view of the syringe and shield assembly shown in FIG. 11, illustrating the position of the snap ring within the grooves.

The main components of the shield according to the subject invention are depicted in FIGS. 2–6. The shield includes a hollow sleeve 20 as shown in FIGS. 2 and 3. The hollow sleeve 20 is mounted to the housing of a syringe (see FIGS. 7–9). The sleeve 20 has two radially extending projections 24 and a groove 22 at one end, into which a flexible snap ring 32 (see FIG. 5) can be inserted. In an alternate embodiment of the hollow sleeve shown in FIG. 4, the groove 28 is not located at an end of the hollow sleeve 26 and only one radially extending projection 30 is utilized. The mounting of this embodiment of the hollow sleeve 26 to the housing of a syringe is shown in FIGS. 10–12. Generally, a single projection (and corresponding slot as discussed below) is most suitable on small syringes such as insulin syringes. The double projection is most suitable for larger, i.e., 3 cc or greater, syringes. It should be readily apparent, however, that one or more projections and corresponding slots can be utilized on any size syringe despite these preferences.

The shield assembly also includes a flexible snap ring 32 as shown in FIG. 5. Preferably, the snap ring is C-shaped and square or rectangular in cross-section. The size of the snap ring is such that tensional forces hold it within the groove of the hollow sleeve and the interior wall of the needle shield (see below). As a result, when the snap ring becomes aligned with the groove in the interior wall of the needle shield, it extends outward (at the tips of the "C").

Figures 6, 8, 9:
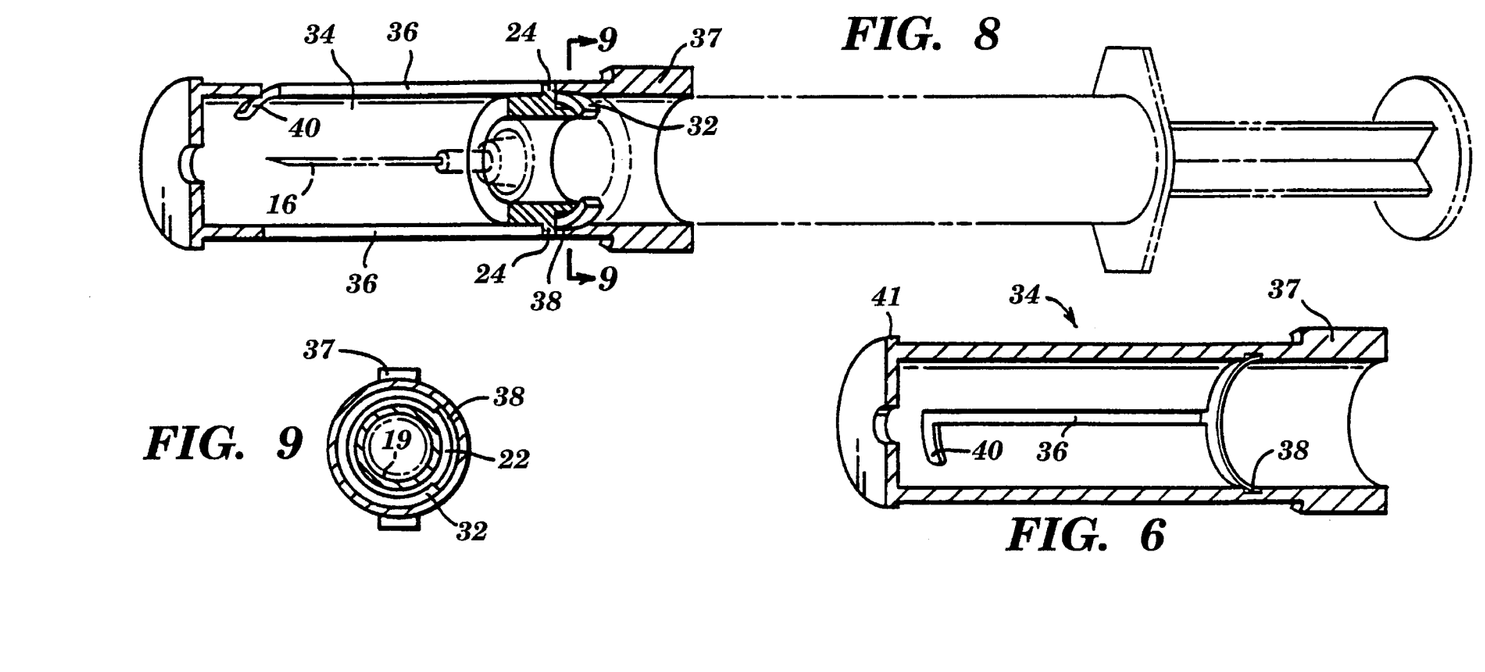
FIG. 6 is a partially cut-away isometric view of one embodiment of a needle shield according to the subject invention.
FIG. 8 is a partially cut-away isometric view of the syringe and shield assembly shown in FIG. 7 with the needle shield in an extended position.
FIG. 9 is a cross-sectional view of the syringe and shield assembly shown in FIG. 8, illustrating the position of the snap ring within the grooves.

A needle shield is also included in the shield, as shown in FIG. 6. The needle shield 34 is tubular and preferably closed on one end, except for a hole which allows insertion of a needle. The closed end helps to contain any blood which may drip from the needle or syringe assembly after use. The hole or aperture for insertion of a needle is small and does not permit insertion of hands or fingers, which helps prevent needle sticks or contact. The closed end may be preformed or the end may be a cap-type that is snapped onto the end. In a further embodiment of the present invention, the end of the needle shield may be open.

The needle shield has one or more longitudinally extending slots 36 on the interior wall thereof and an interior groove 38 at one end of the slots. The groove 38 allows extension of the snap ring when the needle shield is extended, locking into place and preventing further movement of the needle shield. Each of the radially extending projections of the hollow sleeve are slidably disposed within a corresponding slot, so that the needle shield can slide to an extended position to surround and shield the needle or to a retracted position surrounding the syringe housing and leaving the needle exposed for use. By placing the slot and groove on the interior of the needle shield, they cannot be tampered with. However, the shield will function if the slots and groove extend through the exterior surface of the needle shield, and this is also encompassed by the subject invention. The needle shield also has an aperture through the side thereof the size of the cross-section of the snap ring, positioned over the location of the hollow sleeve's groove when the needle shield is fully retracted. This aperture allows assembly of the shield components when a closed end needle shield is utilized. The hole is not necessary for assembly when the end of the needle shield is open, as discussed below.

A temporary locking means for releasably locking the needle shield in its retracted position can also be included. This prevents premature extension of the needle shield which would result in the locking of the shield into place over the needle, preventing use. As shown in FIG. 6, the temporary locking means preferably comprises one or more notches 40 formed in the interior of the needle shield extending off the ends of the slots. These notches are disposed substantially transversely relative to the slots, and are sized to receive the projections of the hollow sleeve. Rotation of the needle shield so that the projections are positioned within the notches prevents extension of the needle shield.

The needle shield can also be provided with a ring or lip 41 at its base (the end nearest the syringe needle) to help prevent slippage of a user's hand over the end of the shielding means to the needle. Slippage is also prevented by the finger grips 37 which allow a firm grasp on the needle shield during movement thereof.

The use of the needle shield, including the hollow sleeve, the needle shield, and the snap ring, is shown in FIGS. 7–12. The syringe is as shown in FIG. 1.

Figure 7:
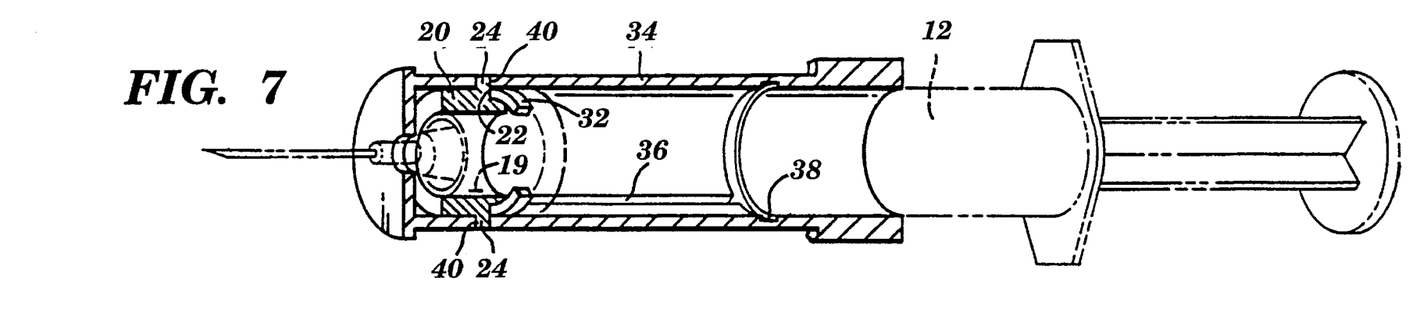
FIG. 7 is a partially cut-away isometric view of a syringe and shield assembly according to one embodiment of the subject invention, with the needle shield in a retracted position.

Referring to FIG. 7, the hollow sleeve 20 (see FIGS. 2 and 3) is mounted to the front restricted end 19 of the syringe. The needle shield 34 (see FIG. 6) is shown in the retracted position, with the snap ring 32 positioned in the groove 22 of the hollow sleeve 20. The projections 24 of the hollow sleeve 20 are temporarily locked in the notches 40 of the needle shield 34 extending off the ends of the slots 36.

Referring to FIG. 8, the needle shield 34 has been rotated and moved forward, allowing the projections 24 to be guided along in the corresponding slots 36. The extension of the needle shield 34 over the needle 16 has positioned the snap ring 32 in line with the interior groove 38 of the needle shield 34. As shown in FIG. 9, the snap ring 32 has extended to occupy both the groove 22 of the hollow sleeve and the groove 38 of the needle shield. This permanently locks the position of the needle shield.

Referring to FIG. 10, an alternate embodiment utilizing the single projection hollow sleeve 26 of FIG. 4 is shown. The hollow sleeve 26 is also positioned on the housing 12, but not on the restricted end. The needle shield 34 is shown in the retracted position, and in the extended position in FIG. 11. As shown in FIG. 12, the snap ring 32 extends to within the groove 38 of the needle shield from the groove 28 of the hollow sleeve. Since the hollow sleeve 26 is mounted on the housing 12, the housing 12 can be seen in this cross-sectional view.

Having thus described the components of the subject invention, it can be assembled as follows. In one embodiment, the hollow sleeve is mounted to the restricted end of the syringe. The hollow sleeve/housing is then inserted into the open end of the needle shield (one end of the needle shield is closed except for a small aperture for insertion of a needle). The diameter of the needle shield fits snugly about the syringe housing, but leaves enough room for passage of the projections. The projections are passed along the top part of the needle shield until they are disposed within their corresponding slots. To provide an even snugger fit of the needle shield and the syringe housing, the slots on the interior of the needle shield can be extended to the end of the needle shield to allow for insertion of the projections during assembly. The syringe can then be slid along the needle shield, using the projections within the slots as a guide. When the projections reach the end of the slots, the groove of the hollow sleeve is positioned beneath the hole or aperture in the needle shield. The snap ring is then inserted through the hole and into the hollow sleeve's groove. The syringe and shield assembly is then ready for use, once a needle is attached to the syringe. Any full extension of the needle shield will result in the locking of the snap ring into the groove of the needle shield. The needle shield will thus be locked in a position which covers and shields the needle of the syringe.

Alternatively, a needle shield which is open on both ends, at least for assembly, can be utilized. In this embodiment, the syringe is inserted into the needle shield from the end. The needle shield is somewhat shorter than the syringe, and is positioned so that the restricted end of the syringe is exposed. The hollow sleeve is then attached to the syringe housing by suitable means (see above). After the hollow sleeve is attached, the snap ring is inserted into the groove of the hollow sleeve as the hollow sleeve is pulled within the needle shield. In this embodiment, an aperture for insertion of the snap ring is not necessary. However, one could also be utilized if the hollow sleeve is first slid into the needle shield before the snap ring is positioned. The syringe and shield assembly is then ready for use, once a needle is attached to the syringe. If desired, a cap can then be secured over the open end of the needle shielding device. As in the previous embodiment, a small hole or aperture in the cap would allow mounting of a needle to the syringe for use.

Figure 13:
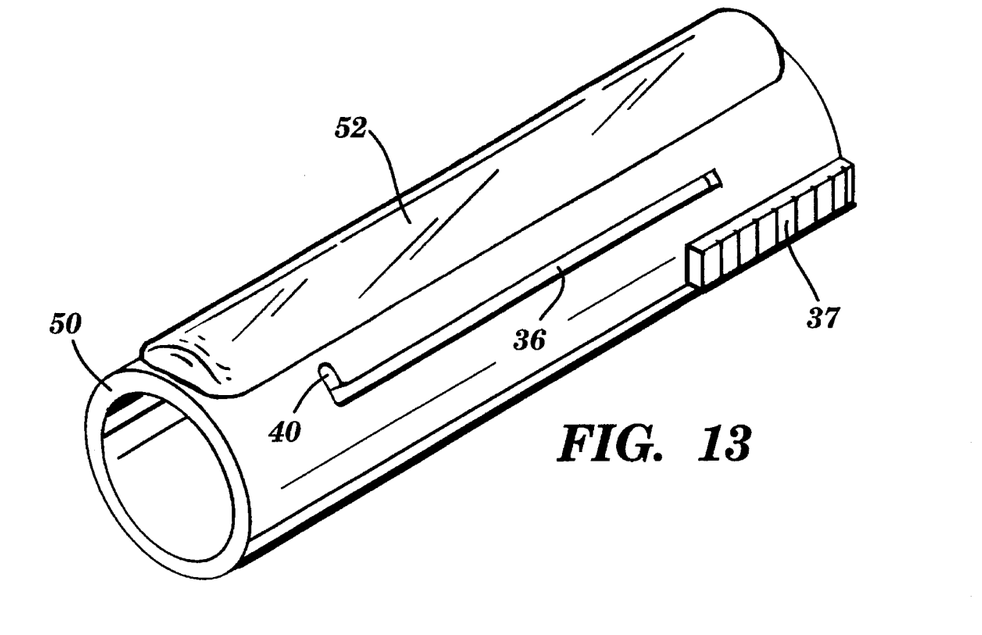
FIG. 13 illustrates an alternate embodiment of a needle shield in accordance with the present invention, illustrating an elongated, convex magnifying arrangement for enlarging the dosage indicia imprinted on the housing of an enclosed syringe.
Figure 14:
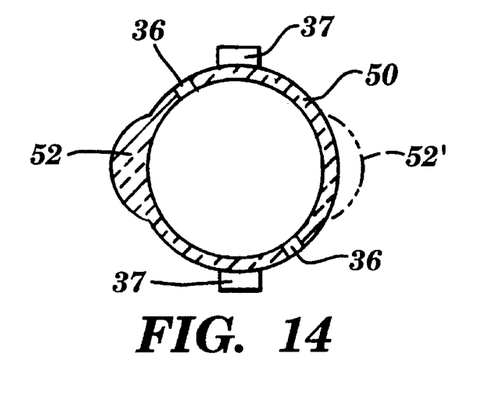
FIG. 14 is a cross-sectional view of the needle shield illustrated in FIG. 13.
Figure 16:
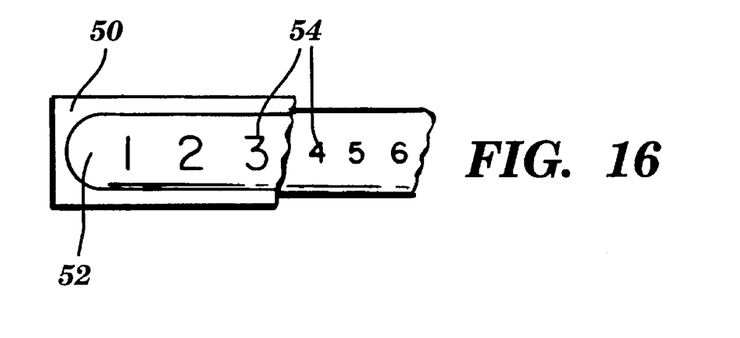
FIG. 16 illustrates the indicia magnification provided by the magnifying arrangement of the present invention.

Referring now specifically to FIGS. 13 and 16, there is illustrated a needle shield 50 incorporating an elongated, convex magnifying arrangement 52 for enlarging the dosage indicia 54 imprinted on the housing of an enclosed syringe. With the exception of the magnifying arrangement 52, the needle shield 50 is generally constructed as detailed above, including at least one longitudinally extending slot 36 and associated notch 40, and finger grips 37.

As illustrated in FIG. 16, the magnifying arrangement 52 preferably provides a magnification of between 1.8×–2.2×. Of course, if required (or desired), less or more magnification may be utilized to enlarge the dosage indicia 54 to a more easily readable size. Preferably, the magnifying arrangement 52 extends longitudinally along substantially the entire length of the needle shield 50, thereby magnifying an elongated section of an underlying syringe when the needle shield 50 is in a retracted position. Again, the length of the magnifying arrangement 52 may be altered as necessary in accordance with the characteristics of the dosage indicia, the orientation of the dosage indicia on the body of a syringe and other relevant factors. When the needle shield 50 is in an extended position in a manner similar to the needle shield 34 illustrated in FIG. 8, the magnifying arrangement 52 is no longer positioned over the dosage indicia 54. As should be readily apparent, in such an extended position, the dosage indicia 54 is no longer enlarged by the magnifying arrangement 52.

A cross-sectional view of a first embodiment of the needle shield 50 is illustrated in FIG. 13. In this embodiment, the elongated, convex magnifying arrangement 52 is formed unitarily with the needle shield 50. If dosage indicia is disposed on opposing sides of a syringe, an additional magnifying arrangement 52', of similar construction, may be incorporated into the needle shield 50.

Figure 15:
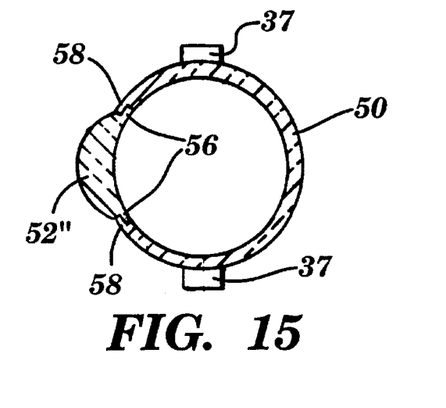
FIG. 15 is a cross-sectional view of a needle shield incorporating a further embodiment of the indicia magnifying arrangement.

A needle shield 50, including an insertable magnifying arrangement 52", is shown in cross-section in FIG. 15. The magnifying arrangement 52" includes a pair of flanges 56 which are slidably insertable within corresponding slots 58 in the needle shield 50. The magnifying arrangement 52" may be fixedly secured within the slots 58 with glue or the like, thereby providing a fixed magnification, or may be removably inserted therein. Advantageously, a user may adjustably control the magnification provided by the instant invention by attaching a magnifying arrangement 52" having a desired magnification to the needle shield 50.

Figure 17:
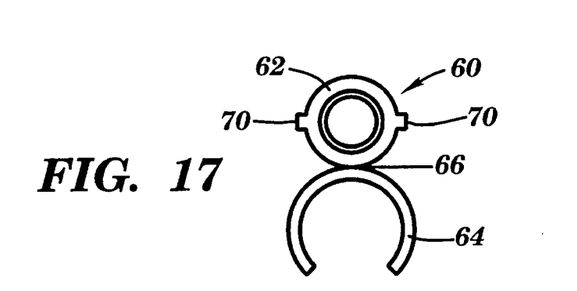
FIG. 17 is a front elevational view of an adapter for attaching the needle shield of the present invention to virtually any type of conventional syringe.
Figure 18:
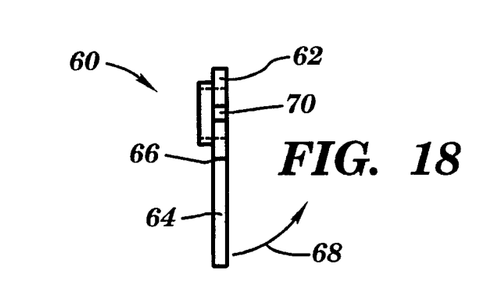
FIG. 18 is a side elevational view of the adapter shown in FIG. 17.

Referring now to FIGS. 17 and 18, there is illustrated an adapter, generally designated as 60, which allows the needle shield 34 (or 50) to be used with virtually any type of conventional syringe (e.g., the syringe illustrated in FIG. 1). The adapter 60 includes a tubular collar 62 designed to fit over the restricted end 19 of the syringe, and a flexible snap ring 64 designed to expand into the groove 38 in the needle shield 34 as the needle shield is longitudinally displaced (i.e., extended) over the hollow syringe needle 16. As previously described with regard to the operation of the flexible snap ring 32, the needle shield 34 is permanently locked over the hollow syringe needle 16 when the flexible snap ring 64 expands into the groove 38. Unlike the loose snap ring 32 of the previous embodiments, however, the flexible snap ring 64 is permanently joined to the tubular collar 62 by a "living" hinge 66. To attach the adapter 60 about the restricted end 19 of the syringe, the flexible snap ring 64 is pivoted about the hinge 66 as indicated by directional arrow 68, until the flexible snap ring 64 is substantially coaxial with the tubular collar 62. Preferably, the components of the adapter 60 are molded unitarily from any suitable material such as plastic or the like.

The tubular collar 62 includes at least one radially-extending projection 70 for engaging a corresponding number of the longitudinally-extending slots 36 on the interior wall of the needle shield 34. Each of the radially extending projections 70 on the tubular collar 62 is slidably disposed within one of the corresponding slots 36, thereby allowing the needle shield 34 to be positioned in an extended position to surround and shield the syringe needle 16, or to be positioned in a retracted position surrounding the syringe housing 12 with the needle 16 exposed for use. If needle shield 50 is used in lieu of shield 34, the magnifying arrangement 52 formed unitarily with the shield 50 enlarges the dosage indicia 54 imprinted on the syringe housing when the shield 50 is in a retracted position.

The adapter 60 of the present invention allows the needle shield 34 to be used in conjunction with a wide variety of conventional-type syringes. One such syringe is the Luer-Lock syringe 72 illustrated in FIGS. 19-20. As known in the art, the restricted end 19 of a Luer-Lock syringe is provided with a series of internal grooves (not shown) into which corresponding ridges (not shown) on needle bracket 17 are twisted to secure the needle bracket 17 to the syringe housing 12. The Luer-Lock syringe is available in many sizes, each having a similarly-sized restricted end 19, thereby allowing an adapter 60 of a given size to be used together with a wide range of sizes of Luer-Lock-type syringes.

To secure the adapter 60 over the restricted end 19 of the Luer-Lock syringe 72, the flexible snap ring 64 (or tubular collar 62) is pivoted about the hinge 66 until the flexible snap ring 64 and the tubular collar are arranged coaxially. Thereafter, the restricted end 19 of the Luer-Lock syringe 72 is inserted through the snap ring 64 and tubular collar 62, in order, until the flexible snap ring 64 is disposed adjacent the housing 12 of the syringe 72 (see FIGS. 19 and 20). Preferably, a snug fit is obtained between the tubular collar 62 and the restricted end 19 by ensuring that the inside diameter of the tubular collar 62 is substantially equivalent to the outside diameter of restricted end 19. Any suitable means (e.g., glue) may be used to permanently secure the tubular collar 62 about the restricted end 19 of the syringe 72.

The needle shield 34 is preferably attached to the syringe/adapter assembly in a manner similar to that disclosed with regard to the previously-described embodiments of the present invention. Once assembled, again referring to FIGS. 19 and 20, the radially-extending projections 70 slidably engage a corresponding number of the longitudinally-extending slots 36 on the interior wall of the needle shield 34, thereby allowing the needle shield 34 to be displaced between retracted and extended positions. As the needle shield 34 is extended over the syringe needle 16, the flexible snap ring 32 comes into alignment with the groove 38 formed in the interior of the needle shield 34. Once properly aligned, the flexible snap ring 64 extends into the groove 38, permanently locking the needle shield 34 over the syringe needle 16. It should be noted that, prior to use, the needle bracket 17 and syringe needle 16 are attached to the restricted end 19 of the syringe in a manner known in the art. Such attachment is accomplished independently of, and without interference from, the adapter assembly 60.

Figure 21:
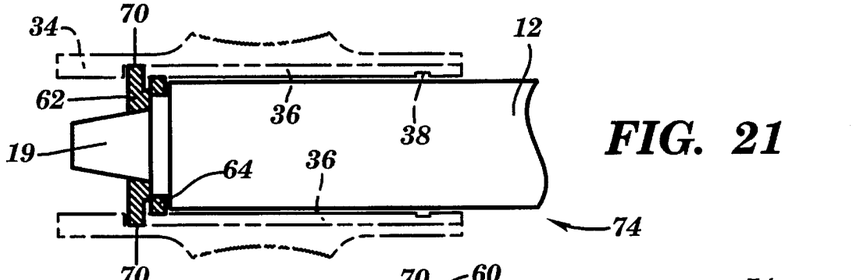
FIG. 21 is a partial cross-sectional view of a syringe and shield assembly, wherein the adapter of FIG. 17 is used to attach a needle shield to a Luer-Slip-type conventional syringe.

The adapter 60 can be used together with other types of conventional syringes. For example, as illustrated in FIG. 21, the adapter can be used in conjunction with a conventional Luer-Slip-type syringe 74. Unlike the previously-described Luer-Lock syringe 72, however, a friction-fit is used to secure a needle bracket (not shown) over the restricted end 19 of the Luer-Slip syringe 74.

The adapter 60 is secured around the restricted end 19 of the Luer-Slip syringe 74 by pivoting the flexible snap ring 64 (or tubular collar 62) about the hinge 66 until the flexible snap ring 64 and the tubular collar are arranged in a coaxial manner, and by inserting the restricted end 19 of the syringe 74 sequentially through the flexible snap ring 64 and tubular collar 62. Again, the adapter 60 is positioned on the restricted end 19 so that the flexible snap ring 64 is positioned adjacent the housing 12 of the syringe 72. A needle bracket can then attached about the restricted end 19 of the syringe in a conventional manner. After the needle shield 34 has been attached to the syringe/adapter assembly, the radially-extending projections 70 on the tubular collar 62 of the adapter 60 slidably engage a corresponding number of the longitudinally-extending slots 36 on the interior wall of the needle shield 34, again allowing the needle shield 34 to be displaced between a retracted and an extended, lockable position.

Figures 22, 23, 24, 25:
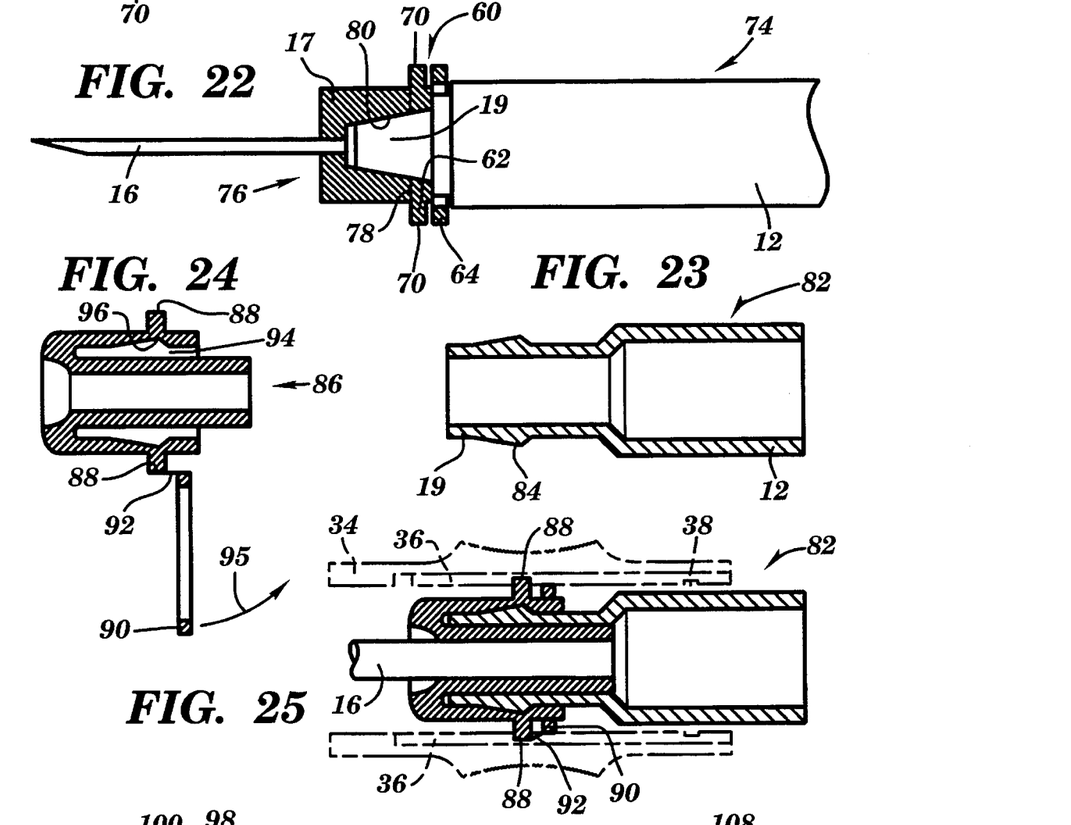
FIG. 22 is a partial cross-sectional view of a syringe and shield assembly utilizing a second embodiment of an adapter in accordance with the present invention, wherein the adapter is formed integrally with a needle bracket, and wherein the adapter/needle bracket combination is secured to a Luer-Slip-type conventional syringe.
FIG. 23 illustrates, in partial cross-section, the restricted end of a "permanent"-type syringe typically used for administering insulin.
FIG. 24 is a cross-sectional view of an adapter/needle bracket combination (sans needle) in accordance with another embodiment of the present invention, wherein the adapter/needle bracket is designed for use with the permanent-type syringe shown in FIG. 23.
FIG. 25 illustrates the adapter/needle bracket (with needle) of FIG. 24 secured over the restricted end of the permanent syringe shown in FIG. 23.

In FIG. 21, the adapter 60 is formed independently of the needle bracket. In FIG. 22, however, the adapter 60 and needle bracket 17 (including needle 16) have been combined as a single adapter/bracket assembly 76 for attachment over the restricted end 19 of a Luer-Slip-type syringe 74. The adapter 60 and needle bracket 17 may be formed unitarily using conventional molding processes, or may be permanently joined (as indicated by dotted line 78) in any suitable manner. In either case, the flexible snap ring 64 is pivotally attached to the remainder of the assembly 76 via the previously-described "living" hinge 66.

The adapter/bracket assembly 76 is attached to the restricted end 19 of the Luer-Slip syringe 74 by inserting the restricted end 19 of the syringe into cavity 80 through the flexible snap ring 64. The needle shield 34 can then be coupled to the assembly 76, with the radially-extending projections 70 again engaging a corresponding number of the longitudinally-extending slots 36 on the interior wall of the needle shield 34. Once again, the needle shield 34 is displaceable between a retracted and an extended, lockable position on the housing 12 of the syringe.

The restricted end 19 of a permanent-type syringe 82, such as those typically used to self-administer insulin, is illustrated in FIG. 23. As is well known in the art, the restricted end 19 of a permanent-type syringe 82 generally includes a locking mechanism 84 for permanently engaging a complementary locking mechanism formed on a permanent-type needle bracket (not shown). As shown in FIG. 23, the locking mechanism 84 on syringe 82 can include, for example, a circumferential ridge designed to engage a corresponding groove (not shown) on a permanent-type needle bracket.

A permanent-type needle bracket 86 (without needle) in accordance with the present invention is illustrated in FIG. 24. Unlike conventional permanent-type needle brackets, needle bracket 86 unitarily incorporates the components of the above-described adapter 60. Specifically, the needle bracket 86 includes at least one radially-extending projection 88, a flexible snap ring 90, and a hinge 92 for pivotally joining the needle bracket 86 and the flexible snap ring 90.

With the exception of the projections 88, flexible snap ring 90, and hinge 92, the needle bracket 86 is configured in a known manner for permanent attachment to the restricted end 19 of a permanent-type syringe 82. The needle bracket 86 includes an annular slot 94 designed to receive the restricted end 19 of the permanent-type syringe 82 therein, with the locking mechanism 84 engaging a corresponding circumferential groove 96 formed within the annular slot 94. Prior to attaching the needle bracket 86 over the restricted end 19 of the permanent-type syringe 82, the flexible snap ring 90 is pivoted about the hinge 92 until the snap ring 90 is disposed about the body of the needle bracket 86 adjacent the radially-extending projections 88. The pivoting of the snap ring 90 is depicted by directional arrow 95 in FIG. 24. The connection of the needle bracket 86 (with needle 16 attached thereto) is illustrated in detail in FIG. 25.

Once again, the radially-extending projections 88 and the flexible snap ring 90 cooperate to selectively lock a needle shield 34 over the needle 16 of a permanent-type syringe 82. As illustrated in FIG. 25, the radially-extending projections 88 slidably engage a corresponding number of the longitudinally-extending slots 36 on the interior wall of the needle shield 34, thereby allowing the needle shield 34 to be displaced between a retracted (needle exposed) and extended (needle shielded) position. To lock the needle shield 34 over the needle 16, a user displaces the needle shield longitudinally over the needle 16 until the flexible snap ring 90 expands into the interior groove 38 of the needle shield 34.

Figure 26:
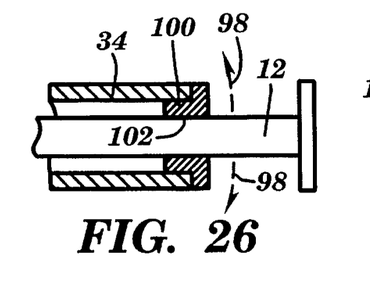
FIG. 26 is a partially cut-away, cross-sectional view of a bushing designed to prevent a syringe from "wobbling" within the needle shield.

The needle shield 34 of the present invention may be used together with a wide range of syringe sizes. In some cases, however, the outside diameter of a syringe housing 12 may be substantially smaller than the inside diameter of the needle shield 34. To prevent the posterior end of the needle shield 34 from "wobbling" (directional arrow 98) relative to the syringe housing 12, the present invention provides a unique bushing 100 which is designed to center the syringe housing 12 within the needle shield 34 so that the longitudinal axis of the syringe housing 12 is substantially parallel to the longitudinal axis of the needle shield 34. In its preferred embodiment, as illustrated in FIG. 26, the bushing 100 is formed as a tubular plug which is designed to be inserted within the posterior end of the needle shield 34. To allow the needle shield 34 to be extended/retracted as discussed above, the diameter of the bore 102 of the bushing 100 is slightly larger than the outside diameter of the syringe housing 12. The bushing 100 may be permanently inserted into the needle shield 34 using glue or the like, or may be attached thereto using a friction fit. Of course, the actual size of the bushing 100 is dependent upon the relative sizes (e.g., diameters) of the syringe housing 12 and the needle shield 34.

Figure 27:
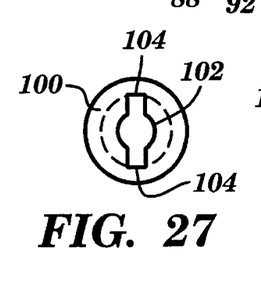
FIG. 27 is a first embodiment of the bushing shown in FIG. 26.

The bushing 100 may be attached to the posterior end of the needle shield 34 either before or after the shield 34 has been attached to a syringe using the adapter 60. FIG. 27 illustrates an embodiment of the bushing 100 which is secured to the needle shield 34 before the shield 34 is attached to a syringe. The bore 102 of the bushing 100 includes at least one slot 104 designed to accommodate the radially-extending projections 70 on the adapter 60 as a syringe having the adapter 60 previously attached thereto is inserted through the needle shield 34 during assembly.

Figure 28:
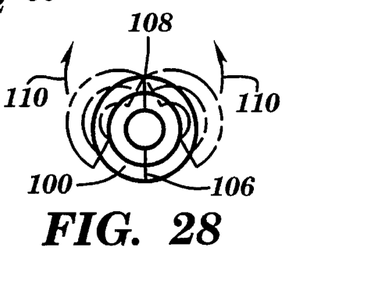
FIG. 28 is a second embodiment of the bushing shown in FIG. 26.

FIG. 28 illustrates an embodiment of the bushing 100 which is inserted into the posterior end of the needle shield 34 after the shield has been suitably attached to a syringe via adapter 60. In this case, the bushing 100 is fully split at point 106 allowing the opposing halves of the bushing to be spread apart at point 108 as depicted by directional arrows 110. The bushing may be partially split at point 108 as illustrated in FIG. 28 or may remain unsplit, depending upon the characteristics of the material used to form the bushing.

Attachment to the needle shield 34 is accomplished by spreading apart the opposing halves of the bushing, and by inserting the syringe housing 12 therebetween. The halves of the bushing 100 are then closed and the bushing is displaced along the syringe housing 12 until it engages the posterior end of the needle shield (as shown in FIG. 26). One again, the bushing 100 may be permanently inserted into the needle shield 34 using glue or the like, or may be attached thereto using a friction fit.

Figure 19:
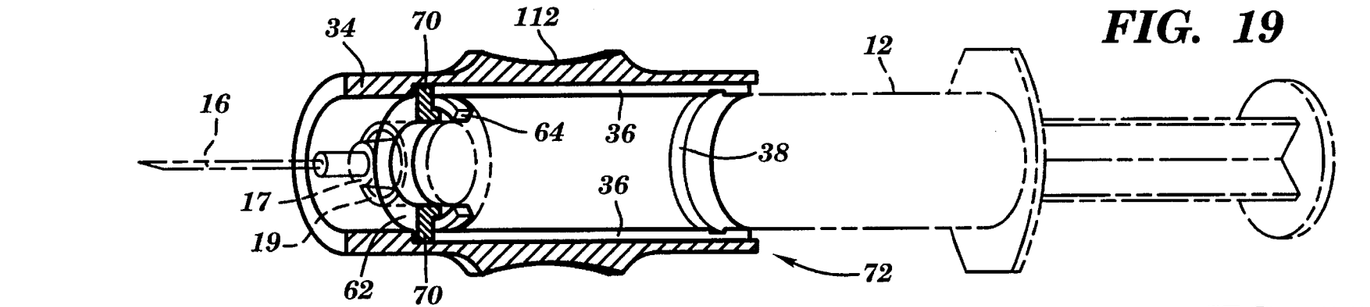
FIG. 19 is a partially cut-away isometric view of a syringe and shield assembly, wherein the adapter of FIG. 17 is used to secure a needle shield, such as that illustrated in FIG. 6, to a Luer-Lock-type conventional syringe, and wherein the needle shield is in a retracted position.
Figure 20:
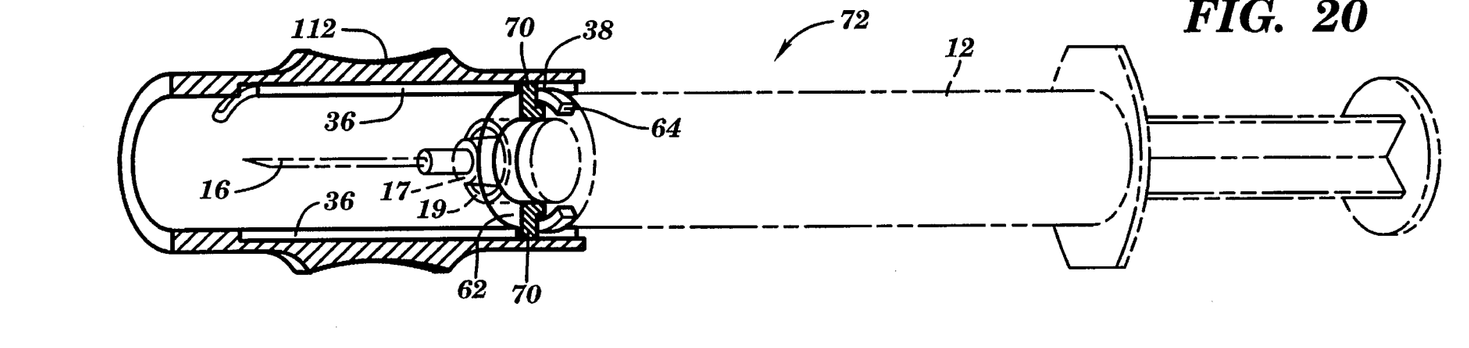
FIG. 20 is a partially cut-away isometric view of the syringe and shield assembly shown in FIG. 19, with the needle shield in an extended position.

As illustrated in FIGS. 19–20, the needle shield 34 of the present invention may further include at least one arcuate, knurled, finger grip 112. Advantageously, a user's fingers remain within the depression of each arcuate finger grip 112 during an operational displacement of the needle shield, further preventing accidental needle sticks.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

We claim:

1. A syringe assembly comprising:

a syringe housing having a main body and a restricted end;

a needle attached to the restricted end of said syringe housing;

a flexible snap ring mounted about the restricted end of said syringe housing;

a tubular collar mounted about the restricted end of said syringe housing adjacent said flexible snap ring, said tubular collar including at least one radially extending projection;

hinge means for pivotally securing said flexible snap ring to said tubular collar, said flexible snap ring, tubular collar and said hinge means forming an adapter assembly;

means for shielding said needle;

at least one longitudinally extending slot formed in an interior wall of said needle shielding means, each radially extending projection on the tubular collar of said adapter assembly slidably engaging a corresponding one of said longitudinally extending slots, the engagement between each projection and corresponding slot allowing said needle shielding means to be moved between an extended position surrounding and shielding said needle, and a retracted position in which said needle is exposed for use; and groove means formed about an interior diameter of said needle shielding means, wherein said flexible snap ring extends into said groove means when said needle shielding means is moved to said extended position surrounding and shielding said needle, thereby permanently locking said needle shielding means in said extended position.

2. The syringe assembly according to claim 1, wherein the flexible snap ring, tubular collar and hinge means of said adapter assembly are formed as a single unit.

3. The syringe assembly according to claim 1, further including a needle bracket for attaching said needle to the restricted end of said syringe housing.

4. The syringe assembly according to claim 3, wherein said adapter assembly is disposed on the restricted end of said syringe housing between said needle bracket and the main body of said syringe housing.

5. The syringe assembly according to claim 3 wherein said adapter assembly and said needle bracket are unitary.

6. A method for shielding a needle mounted to a restricted end of a syringe housing, comprising the steps of:

providing an adapter assembly for movably attaching a needle shield to said syringe housing, said adapter assembly including a flexible snap ring, a tubular collar including at least one radially extending projection, and a hinge member for pivotally securing said flexible snap ring to said tubular collar;

pivoting said flexible snap ring relative to said tubular collar about said hinge member until said flexible snap ring and said tubular collar are arranged substantially coaxially;

mounting said adapter assembly to the restricted end of said syringe housing by inserting the restricted end of said syringe housing through said flexible snap ring and said tubular collar;

providing a needle shield having a groove formed about an inside diameter thereof and at least one longitudinally extending interior slot;

movably positioning said needle shield on said syringe housing, with each radially extending projection on the tubular collar of said adapter assembly slidably engaging a corresponding one of said longitudinally extending slots in said needle shield, the engagement between each projection and corresponding slot allowing said needle shield to be moved between an extended position surrounding and shielding said needle, and a retracted position in which said needle is exposed for use; and extending said needle shield to surround and shield said needle, wherein said flexible snap ring extends into said groove when said needle shield is moved to said extended position surrounding and shielding said needle, thereby permanently locking said needle shielding means in said extended position.

7. A syringe assembly comprising:

a syringe including a needle and a housing;

means for selectively shielding said syringe needle;

an adapter assembly for displaceably coupling said needle shielding means to said syringe, said adapter including a flexible snap ring, a tubular collar including at least one radially extending projection, and hinge means for pivotally securing said flexible snap ring to said tubular collar;

at least one longitudinally extending slot formed in an interior wall of said needle shielding means, each radially extending projection on the tubular collar of said adapter assembly slidably engaging a corresponding one of said longitudinally extending slots, the engagement between each projection and corresponding slot allowing said needle shielding means to be moved between an extended position surrounding and shielding said needle, and a retracted position in which said needle is exposed for use; and groove means formed about an interior diameter of said needle shielding means, wherein said flexible snap ring extends into said groove means when said needle shielding means is moved to said extended position surrounding and shielding said needle, thereby permanently locking said needle shielding means in said extended position.

8. The syringe assembly according to claim 7, wherein the flexible snap ring, tubular collar and hinge means of said adapter assembly are formed as a single unit.

* * * * *